(12) United States Patent
Slack et al.

(10) Patent No.: US 7,919,236 B2
(45) Date of Patent: Apr. 5, 2011

(54) G-PROTEINS

(75) Inventors: Jay Patrick Slack, Loveland, OH (US); Thomas Scott McCluskey, Amelia, OH (US)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 10/538,038

(22) PCT Filed: Dec. 17, 2003

(86) PCT No.: PCT/CH03/00830

§ 371 (c)(1),
(2), (4) Date: Jun. 8, 2005

(87) PCT Pub. No.: WO2004/055048

PCT Pub. Date: Jul. 1, 2004

(65) Prior Publication Data

US 2006/0275765 A1 Dec. 7, 2006

Related U.S. Application Data

(60) Provisional application No. 60/434,790, filed on Dec. 18, 2002.

(51) Int. Cl.
C12Q 1/68 (2006.01)
C07H 21/04 (2006.01)
C12P 21/06 (2006.01)
C07K 14/705 (2006.01)

(52) U.S. Cl. ........ 435/6; 435/69.1; 435/320.1; 435/325; 530/350; 536/23.5

(58) Field of Classification Search .......................... None
See application file for complete search history.

(56) References Cited

U.S. PATENT DOCUMENTS 5,817,759 A * 10/1998 Margolskee .................. 530/350
7,041,457 B2 * 5/2006 Yao et al. ........................ 435/7.1

FOREIGN PATENT DOCUMENTS

WO       WO 0118050        3/2001
WO       WO 02/36622 A     5/2002

OTHER PUBLICATIONS

Ruiz-Avila et al. (PNAS. Jul. 17, 2001. vol. 98; No. 15: 8868-8873).*
Alignment (2011).*
International Search Report dated Jul. 14, 2004 for Application PCT/CH03/00830.
Mody, Sejal M.; "Incorporation of Galphaz-Specific Sequence at the Carboxyl Terminus Increases the Promiscuity of Galpha16 Toward $G_i$ Coupled Receptors", Molecular Pharmacology, Baltimore, MD, US, vol. 57, No. 1, pp. 13-23, Jan. 2000.
Kostenis, Evi, "Is Galpha16 the Optimal Tool for Fishing Ligands of Orphan G-Protein-Coupled Receptors?", Trends in Pharmacological Sciences, Elsevier Trands Journal, Cambridge, GB, vol. 22, No. 11, pp. 560-564, Nov. 1, 2000.
Ueda, Takashi, et al., "Functional Interaction between T2R Taste Receptors and G-Protein Alpha Subunits Expressed in Taste Receptor Cells", Journal of Neuroscience, vol. 23, No. 19, pp. 7376-7380, Aug. 13, 2003.
International Search Report dated Jul. 14, 2004 for Application PCT/CH03/00830.

* cited by examiner

*Primary Examiner* — Scott Long
(74) *Attorney, Agent, or Firm* — Norris, McLaughlin & Marcus, P.A.

(57) ABSTRACT

$G_{\alpha q\text{-}Gustducin}$ chimeric G-proteins that functionally couple to G-protein coupled receptors. The chimeras can be expressed in heterologous cell systems and can be used as the basis of assays for identifying modulators of taste response, in particular bitter, sweet or umami taste responses.

24 Claims, No Drawings

SEQUENCE LISTING

<160> NUMBER OF SEQ ID NOS: 2

<210> SEQ ID NO 1
<211> LENGTH: 1122
<212> TYPE: DNA
<213> ORGANISM: Homo sapiens
<220> FEATURE:
<221> NAME/KEY: CDS
<222> LOCATION: (1)..(1122)

<400> SEQUENCE: 1

```
atggcccgct cgctgacctg gcgctgctgc ccctggtgcc tgacggagga tgagaaggcc      60
gccgcccggg tggaccagga gatcaacagg atcctcttgg agcagaagaa gcaggaccgc     120
ggggagctga agctgctgct tttgggccca ggcgagagcg ggaagagcac cttcatcaag     180
cagatgcgga tcatccacgg cgccggctac tcggaggagg agcgcaaggg cttccggccc     240
ctggtctacc agaacatctt cgtgtccatg cgggccatga tcgaggccat ggagcggctg     300
cagattccat tcagcaggcc cgagagcaag caccacgcta gcctggtcat gagccaggac     360
ccctataaag tgaccacgtt tgagaagcgc tacgctgcgg ccatgcagtg gctgtggagg     420
gatgccggca tccgggcctg ctatgagcgt cggcgggaat tccacctgct cgattcagcc     480
gtgtactacc tgtcccacct ggagcgcatc accgaggagg gctacgtccc cacagctcag     540
gacgtgctcc gcagccgcat gcccaccact ggcatcaacg agtactgctt ctccgtgcag     600
aaaaccaacc tgcggatcgt ggacgtcggg ggccagaagt cagagcgtaa gaaatggatc     660
cattgtttcg agaacgtgat cgccctcatc tacctggcct cactgagtga atacgaccag     720
tgcctggagg agaacaacca ggagaaccgc atgaaggaga gcctcgcatt gtttgggact     780
atcctggaac taccctggtt caaaagcaca tccgtcatcc tctttctcaa caaaaccgac     840
atcctggagg agaaaatccc cacctcccac ctggctacct atttccccag tttccagggc     900
cctaagcagg atgctgaggc agccaagagg ttcatcctgg acatgtacac gaggatgtac     960
accgggtgcg tggacggccc cgaggcagc aacttaaaaa aagaagataa ggaaatctat    1020
tctcacatga cctgcgctac tgacacacaa aacgtcaaat tcgtgtttga tgccgtgaca    1080
gatataataa taaaagagaa cctcaaagac tgtgggctct tc                       1122
```

<210> SEQ ID NO 2
<211> LENGTH: 374
<212> TYPE: PRT
<213> ORGANISM: Homo sapiens

```
<400> SEQUENCE: 2

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
            130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Leu Lys Lys Glu Asp
                325                 330                 335

Lys Glu Ile Tyr Ser His Met Thr Cys Ala Thr Asp Thr Gln Asn Val
            340                 345                 350

Lys Phe Val Phe Asp Ala Val Thr Asp Ile Ile Lys Glu Asn Leu
            355                 360                 365

Lys Asp Cys Gly Leu Phe
    370
```

G-PROTEINS

The invention relates to chimeric G-proteins, and in particular those that mediate in taste receptor transduction pathways. The invention also relates to assays based on heterologous expression systems containing said proteins, and their use in screening for modulators of bitter, sweet and umami taste response in humans.

Taste sensation can be classified into five separate modalities: bitter, salty, sour, sweet and umami. Tastants affect the palatability of food and beverages, thereby influencing human nutritional habits. They also affect the palatability of other ingestibles such as orally administered pharmaceuticals and nutraceuticals. Understanding and manipulating the mechanism of taste transduction has implications for the food and pharmaceutical industries. If the taste transduction pathways can be manipulated, it may be possible to create assays based on heterologous expression systems, which in turn may be used to identify compounds that can modulate taste response, and thereby render certain foods more palatable or increase patient compliance in oral pharmaceutics and nutraceutics.

Much has already been published on the mechanism of taste transduction. The sensation of taste is initiated by the interaction of tastant molecules with their receptors located in the membrane of cells found in the taste buds, which are located in the lingual epithelium of the fungiform, folate and circumvallate papillae as well as in the soft palate and the epiglottis. Recent advances in biochemical and physiological studies have enabled researchers to conclude that sweet, umami and bitter taste transduction is largely mediated by so-called G-protein coupled receptors or GPCRs.

GPCRs are cell surface proteins that are able to bind to tastant molecules whereupon they couple to G-proteins initiating cellular processes producing secondary messengers, such as calcium ions, that enable the cells to send a signal to the brain indicating a taste response. In general, GPCRs are classified as $G_q$-, $G_i$-, $G_o$-, and $G_s$-coupled receptors, which notation is reflective of the primary G-protein effector in their requisite signal transduction pathways. Taste receptors are classified as $G_t$-coupled GPCRs because of their interaction with Gustducin, which is a $G_{\alpha i}$-type G-protein.

The recent identification of genes encoding GPCRs believed to be involved in bitter, sweet and umami taste sensation allows for the development of heterologous expressions systems that can be useful in the identification of chemical molecules that modulate taste transduction pathways. For, example the availability and use of receptors in heterologous expression systems permits of the screening for high affinity agonists, antagonists, inverse agonists and modulators of taste activity. However, there are many technical challenges in developing reliable assays based on an heterologous expression systems. One problem resides in the reliable expression of high concentrations of GPCRs at the surface of a foreign host cell. A second problem is the provision of G-proteins that not only are able to couple with many different types of GPCRs (often, such G-proteins are referred to as "promiscuous"), but also couple with high efficiency, such that even with relatively low surface concentrations of GPCRs, the cell signal is as strong as possible.

With regard to this second problem, the so-called $G_{\alpha q}$ proteins, $G_{\alpha 15}$ and $G_{\alpha 16}$, are known to bind to many classes of GPCRs. Furthermore, they couple GPCRs to the activation of phopholipase C which leads to an increase in intracellular calcium levels. This signaling cascade can be easily and quickly measured by measuring the calcium levels in the cells as is well known in the art (see for example WO 0118050).

However, $G_{\alpha 15}$ and $G_{\alpha 16}$ are not considered to be truly universally promiscuous G-proteins since there are several receptors that are incapable of activating them, see for example, Offermanns, S. and Simon, M., 1995, J. Biol. Chem., 270: 15175-15180; Lee, J. W. M. et al., 1998, J Neurochem., 70:2203-2211); Huang, Y. et al., 1996, J. Biol. Chem. 271:3975-3978.; Wu, D. et al., 1992, J. Biol. Chem. 267: 25798-25802; Wu, D. et al., 1993, Science, 261:101-103; Zhu, X and Bimbaumer, L., PNAS USA, 93: 2827-2831; Parmentier, M. L. et al., 1998, Mol. Pharmacol., 53: 778-786). Furthermore, published literature indicates that most of these GPCRs that are particularly ineffective in activating $G_{\alpha 15}$ and $G_{\alpha 16}$ G-proteins are the $G_i$-type GPCRs (Mody, S. M. et al., 2000, Mol. Pharmacol., 57:13-23).

Thus, since sweet, umami and bitter taste receptors are believed to couple to gustducin (a $G_{\alpha i}$-type G-protein) and the aforementioned studies suggest that, $G_{\alpha 15}$ and $G_{\alpha 16}$ are not the optimal partners for $G_{\alpha i}$-type GPCRs, a skilled person would not expect efficient coupling of activated taste receptors to either $G_{\alpha 15}$ or $G_{\alpha 16}$. On the other hand, Gustducin itself does not offer a practical solution as this G-protein modulates release of cyclic nucleotides (cNMPs) which are not as easily measured as, for example, increases in Calcium ions. It is technically difficult to measure cNMPs and requires an immunoassay that generally takes in the order of 4 to 6 hours, and then only provides an end-point assessment. Still further, it is complicated to use a specialised $G_{\alpha i}$ protein, such as Gustducin in a heterologous cell expression system. To do so, one would have to introduce two additional G-protein sub-units (the beta and gamma sub-units) into the heterologous host cells to fully reconstitute the taste-receptor- G-protein complex. $G_{\alpha 16}$ on the other hand can complex with beta/gamma sub-units endogenous to mammalian cells, such as cells of the HEK 293 cell line. It is faster, easier and more sensititive to employ $G_{\alpha 16}$ rather than $G_{\alpha i}$-type of G-protein such as Gustducin.

There remains a need to develop G-proteins that display high affinity for a wide range of taste receptors and in particular, sweet, umami and bitter receptors, that can be incorporated into heterologous expression system assays to screen for modulators of the human taste response, thereby to quantify the activity of known tastant molecules and to discover new ones.

The use of chimeric G-proteins has been suggested in the prior art. In WO 02/36622 a $G_{\alpha q}$ chimeric protein is describe that is substituted with at least 5 amino acid units from the C-terminus of Transducin. Such Chimeric proteins are described as being more promiscuous than the native $G_{\alpha q}$ in relation to two chemosensory GPCRs. Notably, however, the only taste receptor tested in this reference was a mouse bitter receptor. Therefore, it is not clear whether any of the chimeric G-proteins described would couple more efficiently to human bitter, sweet or umami taste receptors.

Mody S. M. in Molecular Pharmacology 57: 13-23 (2000) describes chimeras of $G_{\alpha 16}$ and a specific sequence of $G_{\alpha z}$ and their increased promiscuity toward $G_i$-coupled receptors. Mody concludes that the chimeric proteins are not universal adaptors for GPCRs, but they are able to improve the recognition of specific sub-sets of GPCRs. Notably, none of the GPCRs in the sub-sets studied included taste receptors.

Surprisingly, we have now found that chimeric G-proteins based on $G_{\alpha q\text{-}Gustducin}$ are able to bind to a wide range of known and putative bitter taste receptors, and sweet and umami receptors with high affinity.

Accordingly the invention provides in a first aspect a $G_{\alpha q\text{-}Gustducin}$ chimeric G-protein.

In a specific embodiment the chimeric $G_{\alpha q\text{-}Gustducin}$ is a $G_{\alpha 15\ or\ 16\text{-}Gustducin}$ protein, more specifically a $G_{\alpha 16\text{-}Gustducin}$ protein.

In a further specific embodiment the G-protein is one wherein at least the last 5 amino acids of the $G_{\alpha q}$ are replaced by a corresponding number of amino acids of Gustducin, more particularly the last 44 amino acid sequences of the $G_{\alpha q}$ is replaced with a 44 amino acid unit of Gustducin.

In a preferred embodiment there is provided a protein having amino acid sequences as set forth in the SEQ ID 2.

Another aspect the invention provides a nucleic acid encoding for a protein as herein above defined.

In a preferred embodiment the nucleic acid comprises the nucleotide sequence set forth in SEQ ID 1.

Whereas the chimeric proteins of the present invention may be formed by making substitutions at the C-terminus of Gustducin, the skilled person will appreciate that other substitutions or mutations may be incorporated into the G-proteins that may affect their promiscuity and/or their degree of coupling to a given receptor, and these variants of the G-proteins form another aspect of the present invention. Furthermore, such substitutions or mutations may be formed without the skilled person having recourse to any inventive activity, simply by using routine techniques in gene technology such as PCR, gene cloning, site-directed mutagenesis or cDNAs, transfection of host cells, and in-vitro transcription. Thereafter, these variants may be screened for functional coupling to receptors.

In a specific embodiment of this aspect of the invention there is provided a variant that is a polypeptide having 80%, preferably 90%, more preferably 95% or greater homology to the sequence as set forth in SEQ ID No. 2.

Other aspects of the invention are an expression vector comprising nucleic acid encoding for chimeric G-proteins defined herein, and host cells transformed or transfected with said vector.

In yet another aspect of the invention there is provided a method of producing a chimeric G-protein as defined comprising the step of culturing host cells as defined having contained therein an expression vector encoding for the chimeric G-protein, under conditions sufficient for expression of said G-protein, thereby causing production of the protein, and recovering the protein produced by the cell.

In still another aspect of the invention there is provided a method of analysis and discovery of modulators of taste receptors, in particular bitter, sweet, and umami receptors, using the chimeric proteins defined herein.

In a specific embodiment a mammalian cell-based assay employing a transiently transfected gene or cDNA encoding a chimeric protein of the invention and a taste receptor, in particular a bitter, sweet or umami receptor, the method comprising the steps of contacting a compound with the cells, and determining the functional effects of the compound on the receptor: chimeric G-protein complex, such as an increase in cytosolic secondary messengers.

In another specific embodiment of this aspect, the invention is directed to a mammalian cell-based assay using a stably-expressed gene or cDNA.

In yet another specific embodiment, the invention is directed to a mammalian cell-based assay wherein the cells stably express both the receptor and the chimeric G-Protein, preferably in inducible form.

In yet another aspect of the invention, there is provided a compound, or collection of compounds containing the compound, that acts to modulate taste response of taste receptors, in particular bitter, sweet or umami receptors, for use in an assay method defined herein.

In still another aspect of the invention there is provided a compound, or collection of compounds containing the compound that is identified as a modulator of taste response using the assay method described herein, and foods beverages or oral pharmaceutical or neutraceutical preparations containing same.

The various aspects of the present invention will be further described herein with reference to the detailed description, sequence listing and Examples.

DETAILED DESCRIPTION OF THE INVENTION

Well established transient expression systems, which are discussed in more detail below, may be employed to establish the ability of the chimeric G-proteins of the present invention to couple with GPCR taste receptors, and in particular bitter taste receptors, sweet and umami receptors.

Cells expressing both a G-protein of the invention and a GPCR may be contacted with known tastant compounds.

Examples of bitter tastant compounds that may be used in the present invention are selected from the group consisting of Acteoside, Adhumulone, Adlupulone, Aesculetin, Aesculin, L-Alanine, L-alanyl-L-alanyl-L-Alanine, L-alanyl-L-isoleucyl-Alanine L-, L-valyl-L-valyl-Amarogentin, Amaropanin Amaroswerin, Amygdalin, Angustifoline, Antiacetylhumulone, Antiisohumulone, Arginine, L-Arginyl Leucine, Arginyl Leucy Leucine, Arginyl Proline, Asaronaldehyde, Aspartyl Aspartic acid, Asparasaponin I, Atropine, Benzyl beta-D-arabinoside, Benzyl beta-L-arabinoside, Benzyl beta-D-fructoside, Benzyl beta-D-galactoside, Benzyl alpha-D-glucoside, Benzyl beta-D-glucoside, Benzyl alpha-D-mannoside, Bitter Peptides, Bitter Peptides from Soy Proteins, Butyl alpha-D-glucoside, Butyl beta-D-glucoside, Caffeine, Carnosifloside II, Carnosifloside III, Camosifloside IV, Catechin, Epicatechin, Epicatechin gallate, Chaconine, alpha-Chaconine, beta2-Chloramphenicol, Cholic Acid, Cichoriin, Cohumulone, Colupulone, Cryptochlorogenic Acid, gamma-lactone, Cucurbitacin B, Cucurbitacin D, Cyclo Alanine-glycine, Cyclo Alanine-phenylanaline, Cyclo Alanine-valine, Cyclo(L-arginylglycyl-L-prolyl-L-prolyl-L-phenylalanyl-L-isoleucyl-L-valyl), Cyclo Asparagine-phenylalanine, Cyclo Glycine-phenylalanine, Cycloheximide Cyclo Lucine-Tryptophan, Cyclopent(b)azepin-8(1H)-one, 7-Methyl-2,3,6,7-Tetrahydro-Cyclopent(b)azepin-8(1H)-one, 2,3,6,7-tetrahydro-7-hydroxy-7-methyl-Cyclopent-2-en-1-one, 2,5-dihydroxy-5-methyl-3-(1-piperidinyl)-Cyclopent-2-en-1-one, 2,5-dihydroxy-5-methyl-3-(1-pyrrolidinyl) Cyclopent-2-en-1-one, 2,3-di-1-pyrrolidinyl-Cyclopent-2-en-1-one, 5-hydroxy-5-methyl-2,3-di-1-piperidinyl-Cyclopent-2-en-1-one, 5-hydroxy-5-methyl-2,3-di-1-pyrrolidinyl-Cyclopent-2-en-1-one, 5-methyl-2,3-di-1-pyrrolidinyl-Cyclopent-2-en-1-one, 5-methylene-2,3-di-1-pyrrolidinyl-Cyclopent-2-en-1-one, 3-methyl-2-(1-pyrrolidinyl)-Cyclo Phenylalanine-aspartic acid, Cyclo Proline-alanine, Cyclo Proline-asparagine, Cyclo Proline-glycine, Cyclo Proline-isolucine, Cyclo Proline-leucine, Cyclo Proline-methionine, Cyclo Proline-phenylalanine, Cyclo Proline-proline, Cyclo Proline-valine, Cyclo Valine-phenylalanine, Cynaratriol, Cynaropicrin, Cynaropicrin, Daidzein, Daidzin Denatonium benzoate, Denatonium saccharide, Dhurrin, Dihydroxybenzoic Acid, 2,3-Dihydroxybenzoic Acid, 2,4-Ethyl b-L-arabinoside, Ethyl alpha-D-Glucoside, Ethyl beta-D-Glucoside, Eustomoroside, Eustomoside, Gallic Acid, Epigallocatechin, Epigallocatechin gallate, Gaudichaudioside F, Gelidoside, Genistein, Genistin, Gentiopicroside, Gentistic Acid, Gentomoside, Geshoidin, 6'-O-beta-D-Glucosylgentiopicroside, ucozaluzanin C, Glutamyl Aspartic Acid, Glutamyl Glutamic Acid, Glycyl Leucine, Goitrin, Gramine, Grosshemin, Haematoxylin Tetramethyl Ether Helicin, Heptadeca-16-ene, 1-Acetoxy-2,4-Dihydroxy-Heptadeca-16-ene, 1,2,4-Trihydroxy-Histidine, L-Hulupone, Humulinone, Humulone, Hydroxybenzoic Acid, 4-Hymenoside A, Hymenoside B, Hymenoside C, Hymenoside D, Hymenoside E, Hyrnenoside F, Isohumulone, cis-Isohumulone, trans-Isoleucine, L-Isolupanine, Isosparteine, beta-Isosparteine, 10,17-Dioxo-beta-Isosparteine, 10-oxo-beta-Lactucin, L-Leucine, L-alanyl-L-alanyl-L-Leucine,N-[(2R)-6-amino-2-[(4S)-2,5-dioxo-4-(phenylmethyl)-1-imidazolidinyl]-1-oxohexyl]-L-leucyl-L-methionyl-N-methyl-L-phenylalanyl-, (4-1)-lactam, L-Leucine, glycyl-L-alanyl-Leucine, L-L-Leucine, N-(N-2-L-leucyl-L-glutaminyl)-L-Leucine, N-(N-L-leucyl-L-aglutamyl)-L-Leucine, N-[N2-[N2-[N-(1-L-leucyl-L-prolyl)-L-phenylalanyl]-L-asparaginyl]-L-glutaminyl]-L-Leucine, N-[N2-[N -(1-L-leucyl-L-prolyl)-L-phenylalanyl]-L-seryl]-L-glutaminyl]-L-Leucine, L-leucyl-L-valyl-Leucy Leucine, Leucyl Phenylalanine, Limonin, Limoninmonolactone, Linamarin, Lotaustralin, Lupine, Lupanine, 13-Hydroxy-Lupanine, 7-hydroxy-Lupinine, Epilupinine Lupoxes B, Lupoxes C, Lupulone, Luputrione, Mellein, 6-Methoxy-Methionine, L-Methyl alpha-L-arabinoside, Methyl beta-L-arabinoside, Methyl beta-D-Glucoside, Methyl alpha-D-Glucoside 2,3-Di-isoleucine, Methyl alpha-D-Glucoside 2,3-Dileucine, Methyl alpha-D-Glucoside 2,3-Di-L-phenylalanine, Methyl alpha-D-Glucoside 2,3-Di-threonine, Methyl alpha-D-Glucoside 2,3-Di-tyrosine, Methyl a-D-mannoside, Methyl beta-L-xylopyranoside, Methyl alpha-D-xyloside, Naringin, Neochlorogenic Acid, gamma-Lactone, Neohesperidin, Nuezhenide, Oleonuezhenide, Oleuropein, Olivieroside A, Olivieroside B, Olivieroside C, Perrottetin H, Phenylalanine, L-Phenyl alpha-D-galactoside, Phenyl alpha-D-glucoside, Phenyl beta-D-glucoside, Phenylthiourea, Phlomisoside II, Piperidine-2-carboxylic acid, 4-[(2-carboxy-2-hydroxyethyl)thio]-Piperidinecarboxylic acid-2, 4[(2-carboxy-2-hydroxyethyl)thio]-Prehumulone, Prelupulone, Propyl beta-D-fructoside, Propyl alpha-D-glucoside, Propyl beta-D-glucoside, Protocatechuic Acid, Prunasin, Pulcherrimine, Quinidine, Quinine, Quinolizinium-7-olate, Ranitidine, Rebaudioside C, Salicin, Salidroside, Scabraside, Scandenoside R5, Sclareolide, Scopolin, Septemfidoside, Seryl Lysyl Glycyl Leucine, Sinapine, Solanine, alpha-Sparteine, Sparteine, 17-oxo-Stevisalioside A, Strychnine, Suavioside C1, Suavioside D2, Suavioside F, Sucrose Octaacetate, Sweroside, Swertiamarin, Swertiapunimarin, Taxiphyllin, TFI (Furostan, beta-D-galactopyranoside), Theaflavin, Theaflavin Gallate A, Theaflavin Gallate B, Tomatidine, Tomatine, alpha-Tricyclodehydroisohumulone, Trifloroside, Trihydroxybenzoic Acid, 2,4,6-Tryptophan, L-Uracil, 6-propyl-2-thio-L-Valine, L-arginylglycyl-L-prolyl-L-prolyl-L-phenylalanyl-L-isoleucyl-(BPla)Valine, and L-Yohimbine.

As examples of sweet tastants, or compounds that modify sweet taste there may be mentioned Theasaponin E1, Acesulfame K, Alitame, Aspartame, CH 401, Dulcin, Erytritol, Guanidine Sweetener, Isomalt, Isomaltosylfructoside, Isoramfinose, NC 174, Neotame, Perillartine, Phenylacetylglycyl-L-Lysine, Saccharin, SC 45647, sodium Cyclamate, Sorbitol, Sucralose, Sucrononic Acid, Suosan, Superaspartame, Methyl alpha-L-arabinoside, Methyl beta-L-arabinoside, Methyl beta-D-Glucoside, Methyl a-D-mannoside, Methyl beta-L-xylopyranoside, Methyl alpha-D-xyloside, Methyl alpha-D-Glucoside 2,3-Di-isoleucine, Methyl alpha-D-Glucoside 2,3-Di-threonine, Methyl alpha-D-Glucoside 2,3-Di-isoleucine, Protocatechuic Acid, Cynarin, Glycyphyllin, Rebaudioside C, Abrusoside A, Abrusoside B, Abrusoside C, Abrusoside D, Abrusoside E, Apioglycyrrhizin, Araboglycyrrhizin, Baiyunoside, Brazzein, Bryodulcoside, Carnosifloside V, Carnosifloside VI, D. cumminsii, Cyclocarioside A, Cyclocarioside I, Dulcoside A, Fluorene-4-alpha,6-dicarboxylic acid, 4-beta, 10-alpha-dimethyl-1,2,3,4,5,10-hexahydor-Gaudichaudioside A, Glycyrrhizic Acid, Hemandulcin, Hemandulcin, 4beta-hydroxy-Hesperitin-7-Glucoside Dihydrochalcone, Huangqioside E, Huangqioside E, 3-Hydroxyphloridzin, Kaempferol, 2,3-Dihydro-6-Methoxy 3-O-Acetate, Mabinlin Maltosyl-Alpha-(1,6)-Neohesperidin Dihydrochalcone, Mogroside IIE, Mogroside III, Mogroside IIIE, Mogroside IV, Mogroside V, 11-Oxo Mogroside V, Monatin, Monellin, Monoammonium Glycyrrhizinate (Mag), Mukurozioside lib, Naringin Dihydrochalcone, Neoastilbin, Neohesperidin Dihydrochalcone (NHDHC), Neomogroside, Osladin, Pentadin, Periandrin I, Periandrin II, Periandrin III, Periandrin IV, Periandrin V, Phlomisoside I, Phlorizin, Phyllodulcin, Polypodoside A, Potassium magnesium calcium glycyrrhizin, Pterocaryosides A, Pterocaryosides B, Quercetin, 2,3-Dihydro-3-O-Acetate, Quercetin, 2,3-Dihydro-6-Methoxy-Quercetin, 2,3-Dihydro-6-Methoxy-3-O-Acetate, Rebaudioside A, Rebaudioside B, Rubusoside, Scandenoside R6, Siamenoside I, Sodium glycyrrhizinate, Steviolbioside, Stevioside, Stevioside, alpha-Glycosyl Suavioside A, Suavioside B, Suavioside G, Suavioside H, Suavioside I, Suavioside J, Thaumatin, Triammonium Glycyrrhizinate (TAG), Trilobatin Selligueain A, Haematoxylin, Maltitol, Mannitol, Methyl alpha-D-Glucoside 2,3-Di-aspartic acid, Benzoic Acid, 2-(4-Dimethylaminobenzoyl)-Benzoic Acid, 2-Hydroxy-4-aminomethyl-Benzoic Acid, 2-(3-Hydroxy-4-Methoxybenzoyl)-Methyl beta-D-fructoside, Methyl alpha-D-galactoside, Methyl beta-D-galactoside, Curculin, Strogin 1, Strogin 2, Strogin 4, Miraculin, Phenylacetic Acid, 3,4-Dimethoxy-Aminobenzoic Acid, 3-Anisic Acid, Benzyl alcoho, 3-Amino-4-n-propoxyl, 3,4-Caffeic Acid, Cinnamic Acid, Dihydroxycinnamic Acid, 2,4-Ferulic Acid, Hydrolyzed Guar Gum, Hydroxyaminobenzoic Acid, 2,4-Nigerooligosaccharides, Sugarcane Bagasse Extract, Dihydroxybenzoic Acid, 2,3-Dihydroxybenzoic Acid, 2,4-Coumaric Acid, p-Dihydroxybenzoic Acid, 3,5-Hydroxybenzoic Acid, 3-Gurmarin, Gymnemasaponin III, Gymnemasaponin IV, Gymnemasaponin V, Gymnemic Acid I, Gymnemic Acid II, Gymnemic Acid III, Gymnemic Acid IV, Hodulcin, Jujubasaponin II, Jujubasaponin III, Propionic Acid, (−)-2-(4-Methoxyphenoxy)-Ziziphin, Ethyl Maltol, Maltol, Butanoic Acid, 2-Oxo-3-Methyl-Alanine, N-(1-Methyl-4-oxo-2-imidazolin-2-yl) Creatinine, Abrusoside E, mono-methyl ester, Lactitol, Periandrinic acid I, monoglucuronide, Periandrinic acid II, monoglycuronide, Xylitol, Tagatose, d-Benzoyloxyacetic acid, 4-Methoxy Huloduloside I, 4-Nitrophenyl a-D-galactoside, 4-Nitrophenyl alpha-D-glucoside, 4-Nitrophenyl beta-D-glucoside, 4-Nitrophenyl alpha-D-mannopyranoside, Urea, (N-(4-cyanophenyl)-N'-((sodiosulfo)methyl)-Chloramphenicol, Chlorogenic Acid, Methyl alpha-D-Glucoside, Methyl alpha-D-Glucoside 2,3-Di-alanine, Methyl alpha-D-Glucoside 2,3-Di-glycine, Methyl alpha-D-Glucoside 2,3-Di-proline, Methyl alpha-D-Glucoside 2,3-Di-valine, Aniline, 2-Butoxy-5-Nitro-Aniline, 2-Ethoxy-5-Nitro-Aniline, 2-Methoxy-5-Nitro-Aniline, 3-Nitro-(+)-Baiyunol-beta-D-gluccoside-alpha-D-glucoside, Aniline, 1,3-Hydroxy-4-methoxybenzylAniline, 2-Propxy-5-Nitro-(P4000)Benzo-1,4-dioxane 2-(3-Hydroxy-4-Methoxyphenyl)-Benzoe-1,3-dioxan4-one 2-(3-Hydroxy-4-methoxyphenyl)-Benzoic Acid, 2-Benzoyl-4-Methoxy-Benzoic Acid, 2-(4-Methoxybenzoyl)-Benzo-1,3 (4H)-xathiane, 2-(3-Hydroxy-4-Methoxyphenyl)-Benzo-1, 4-xathiane 3-(3-Hydroxy-methoxyphenyl)-Butanoic acid, 4-[3,5-dihydroxy-4-[3-(3-hydroxy-4-methoxyphenyl)-1- oxopropyl]phenoxy]-2-hydroxy-monosodium salt, Butanoic acid, 4-[3,5-dihydroxy-4-[3-(3-hydroxy-4-methoxyphenyl)-1-oxopropyl]phenoxy]-3-oxo-monosodium salt,Cyclohexa-diene-1,4 1-Carboxaldehyde-4-(Methoxymethyl)-, (E)oxime Ethylbenzene, beta-(1,3-Hydroxy-4-methoxyben-zyl)-Hespertin Dihydrochalcone, 3'-Carboxy-Hespertin Dihydrochalcone, 3'-Formyl-Isocoumarin, 3,4-Dihydro-3-(3-Hydroxy-4-methoxy)-Perillartine, 8,9-epoxy-Phenyl 3-Hydroxy-4-methoxybenzyl Ether, Phosphonic acid, [3-[3,5-dihydroxy-4-[3-(3-hydroxy-4-methoxyphenyl)-1-oxopro-pyl]phenoxy]propyl] monopotassium salt, Stevioside ana-logue, Sulfamic acid, [2-[3,5-dihydroxy-4-[3-(3-hydroxy-4-methoxyphenyl)-1-oxopropyl]phenoxy]ethyl]-monopotassium salt, Urea, and N-(4-cyanophenyl)-N'-(2-carboxyethyl)-L-Theanine.

As umami tastants there may be mentioned Glutathione, Glutamyl Glutamic Acid, (Z)-6-Dodecen-4-olide, Inosinic acid, Dodec-Z6-en-4-olide, Glutamic Acid, L-Aconitic Acid, N-(1-deoxy-fructos-1-yl) glutamate, hydrolyzed vegetable protein, Methyl alpha-D-Glucoside, 2,3-Di-lysine, Methyl alpha-D-Glucoside 2,3-Di-ornithine, L-Asparagine, L-a-glutamyl-L-a-glutamyl-L-Glutamic acid, L-a-aspartyl-L-a-glutamyl-Glutamyl valine, Wheat gluten hydrolyzate, Aspar-tic acid L-, L-a-aspartyl-L-a-aspartyl-L-a-aspartyl-Docosahexaenoic acid, and (4Z,7Z,10Z,13Z,16Z,19Z)-L-Theanine.

The functional effects of the tastant molecules on the G-protein may be determined by measuring changes in parameters of the transduction pathways such as intracellular IP3 and $Ca^{2+}$, or by other G-protein specific assays such as labeling with GTPγS, according to techniques known in the art and that are described more fully herein below.

Many functional and orphan bitter taste receptors, and sweet and umami receptors are able to couple with the chi-meric G-proteins of the present invention. As bitter receptors, one can mention those so-called T2Rs or TAS2Rs described in Bufe et al in Nature Genetics 32: 397-401, or Chan-drashekar et al. in Cell, 100: 703-711, or Matsunami in Nature, 404: 601-604. Whereas, as sweet or umami receptors one can mention the known T1R receptors as described in Li, X. et al., 2002, *PNAS USA*, 99: 4692-4696; Nelson, G. et al., 2002, Nature, 416: 199-202; and Nelson, G. et al., 2001, Cell, 101:381-390. Still further, the chimeric G-proteins of the present invention are able to elicit a stronger cell reponse when a ligand binds to a given GPCR, compared with the native Gαq proteins and those reported chimeric Gαq pro-teins referred to herein above.

To illustrate this, Mammalian cells, e.g. HEK293T cells transfected with a known functional bitter taste receptor known as TAS2R16 as described and characterised by Bufe (see above reference) and the chimeric G-protein $G_{\alpha 16\text{-}gustducin\ 44}$ of the present invention may be contacted with 5 mM salicin or 5 mM phenyl-beta-D-glucopyranoside (both known bitter tastants) according to the following pro-tocol to elicit a robust fluorescent signal (using Flexstation) that is about 3-times stronger than a reference chimeric G-protein ($G_{\alpha 16\text{-}z44}$), and about 7-times stronger than the wild-type $G_{\alpha 16}$.

The protocol is described in "G-protein coupled receptors (Signal Transduction Series)"; Editors: Tatsuya Haga and Gabriel Berstein, 1st ed., 424 pp.CRC Press—Boca Raton Fla.; September 1999, and may be summarised as follows:
1. Day 0: 96-well plates are seeded with 20K cells per well and maintained at 37 degrees C. overnight in nutritive growth media.
2. Day 1: Cells are transfected using 300 ng of GPCR DNA and 0.6 μl of Lipofectamine 2000 (Invitrogen) per well. Transfected cells are and maintained at 37 degrees C. over-night in nutritive growth media.
3. Day 2: Growth media is discarded and cells are incubated for 1 hour (at room temperature in the dark) with 75 μl of calcium assay solution consisting of 1.5 μM Fluo-4 AM (Molecular Probes) and 2.5 mM probenicid dissolved in a Hanks balanced salts solution (HBSS) that has been supplemented with 10 mM Hepes, 200 μM calcium chlo-ride and 0.1% bovine serum albumin, pH 7.4 at 37 degrees C.
4. 125 μl of wash buffer consisting of 2.5 mM probenicid dissolved in a Hanks balanced salts solution (HBSS) that has been supplemented with 10 mM Hepes, 200 μM cal-cium chloride and 0.1% bovine serum albumin, pH 7.4 at 37 degrees C., is added to each well and the plate is further incubated for 30 minutes at room temperature in the dark.
5. Buffer solutions are discarded and plate is washed 3 times with 100 μl wash buffer and cells are reconstituted in 200 μl of wash buffer and incubated for 15 minutes at 37 degrees C.
6. Plate is placed in a fluorescent microplate reader, for example the Flexstation (Molecular Devices) or the FLIPR (Molecular Devices) and receptor activation is initiated following addition of 20 μl of a 10× concentrated ligand stock solution. Fluorescence is continuously monitored for 15 seconds prior to ligand addition and for 45-75 seconds after ligand addition. Receptor activation levels are defined as by the two following equations: % Activation=(Maxi-mum fluorescence–baseline fluorescence/baseline fluores-cence)*100 or Fluorescence Increase=Maximum Fluores-cence–baseline fluorescence, where baseline fluorescence represents the average fluorescence levels prior to ligand addition.

In another example, HEK293T cells transfected with a known functional bitter taste receptor known as mouse T2R5 (see Chandreshekar et al, in Cell, Vol. 100, 70-711, Mar. 17, 2000) and the chimeric G-protein $G_{\alpha 16\text{-}gustducin\ 44}$ of the present invention were contacted with 10 uM cycloheximide which was able to elicit a robust fluorescence signal that was 5-times stronger than the wild-type $G_{\alpha 16}$.

In another example, HEK293 T-Rex™ cells stably trans-fected with the known functional human bitter taste receptor TAS2R10 (see Bufe et al in Nature Genetics 32: 397-401) and the chimeric G-protein G16-gustducin 44 of the present invention were contacted with 250 uM strychnine, which was able to elicit a robust fluorescence signal.

In another example, HEK293 T-Rex™ cells stably trans-fected with TAS2R38 (a proposed bitter receptor for phe-nylthiocarbamide, see Kim et al. in Science 299, 1221-5 and Bufe et al in Nature Genetics 32: 397-401) and the chimeric G-protein G16-gustducin 44 of the present invention were contacted with 250 uM phenylthiocarbamide, which was able to elicit a robust fluorescence signal. Similarly 250 μM pro-pythiouracil elicited a robust response.

In another example, HEK293 T-Rex™ cells stably trans-fected with TAS2R43 and the chimeric G-protein G16-gust-ducin 44 of the present invention were contacted with 10 μM aristolochic acid, which was able to elicit a robust fluores-cence signal.

In another example, HEK293 T-Rex™ cells stably trans-fected with TAS2R44 and the chimeric G-protein G16-gust-ducin 44 of the present invention were contacted with 10 μM aristolochic acid, which was able to elicit a robust fluores-cence signal.

Still further in another example, HEK293T cells trans-fected with the known functional sweet taste receptor com-plex that is formed by a heterodimer of human TAS1R2 and TAS1R3 (Li, X et al., 2002, *PNAS USA*, 99: 4692-4696; Nelson, G. et al., 2001, Cell, 101:381-390.;) and the chimeric G-protein $G_{\alpha 16\text{-}gustducin\ 44}$, were contacted with either 2.5 mM aspartame, acesulfame K or sucralose, all of which were able to elicit a robust flurorescence signal that was 2-times stronger than the wild-type $G_{\alpha 16}$.

The chimeric constructs may be produced in a manner known per se using Polymerase Chain Reactions. In one embodiment, chimeric constructs may be produced using a bridge overlap PCR mutagenesis strategy as described in Mody S. M. et al, 2000, Mol. Pharmacol., 57:13-23, whereby a primer is designed to anneal with a terminus, e.g. the C-terminus of a $G_{\alpha q}$ and also code for the at least 5 gustducin-derived amino acids. The chimeric products of the PCR may be cloned into a suitable vector, for example pCR2.1-Topo (commercially available from Invitrogen) and submitted for DNA sequencing in order to verify correct replacement of the terminus of the $G_{\alpha q}$.

After verfication of the sequence, chimeric $G_{\alpha q\text{-}Gustducin}$ cDNA fragments may be sub-cloned into a suitable vector, e.g. pcDNA 3.1 mammalian expression vector and transiently transfected in a mammalian host cell, for example HEK293T or HEK T-Rex™ to verify correct expression of the transgene.

After a post-transfection period, e.g. 48 hours, cell lysates may be prepared, analysed by a Western-Blot analysis in order to confirm correct expression of the chimeric proteins. Once correct protein expression is confirmed, suitable mammalian cells, e.g. HEK293T cells or HEK T-Rex™ may be transfected to generate cells stably expressing chimeric $G_{\alpha q\text{-}Gustducin}$ according to techniques well known in the art.

In practising the various aspects and embodiments of the present invention in relation to cloning, elucidating ligand-receptor pairs, and finding modulators of the bitter, sweer or umami response, recourse is made to conventional techniques in molecular biology, microbiology and recombinant technology. Accordingly, the skilled person is fully apprised of such techniques and as such they are hereafter treated only summarily in order to more fully describe the context of the present invention.

In order to express cDNAs encoding the G-proteins or receptors, one typically subclones the appropriate cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the G-protein or receptor-encoding nucleic acid in host cells. A typical expression cassette thus contains a promoter operably linked to the nucleic acid sequence encoding the G-protein or receptor and signals required for efficient polyadenylation of the transcript, ribosome binding sites, and translation termination. The nucleic acid sequence encoding the G-protein or receptor as the case may be, may typically be linked to a membrane-targeting signal such as the N-terminal 45 amino acids of the rat Somatostatin-3 receptor sequence to promote efficient cell-surface expression of the recombinant G-protein or receptor. Additional elements may include, for example enhancers.

An expression cassette should also contain a transcription termination region downstream of the structural gene to provide for efficient termination. The termination region may be obtained from the same gene as the promoter sequence or may be obtained from different genes.

For expression of the G- proteins or receptors, conventional vectors for expression in eucaryotic or procaryotic cells well known in the art may be used. Examples of vectors include, but are not limited to standard bacterial expression vectors including plasmids such as pBR322-based plasmids, pSKF, pET23D, and fusion expression systems such as GST and LacZ.

Expression vectors containing regulatory elements from eukaryotic viruses are typically used in eukaryotic expression vectors, e.g., SV40 vectors, cytomegalovirus vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the G-protein or receptor, which are then purified using standard techniques.

Any of the well known procedures for introducing nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

For example, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon (Hillen and Berens 1994, Annu. Rev. Microbiol. 48, 345-369; Hillen et al., 1983, Control, J. Mol. Biol. 169, 707-721). Tetracycline regulation in the T-Rex™ System is based on the binding of tetracycline to the Tet repressor and derepression of the promoter controlling expression of the gene of interest (Yao et al. 1998, Hum. Gene Ther. 9, 1939-1950).

After the expression vector is introduced into the cells, the transfected cells may be cultured under standard culturing conditions. The G-protein or receptor protein may be recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant G-protein or receptor may be recovered from the culture medium in which the recombinant cells had been cultured.

The activity of a receptor in binding to ligands, and the coupling of the G-protein to the receptor may be assessed using a variety of in vitro and in vivo assays to determine functional, chemical, and physical effects, e.g., measuring ligand binding, secondary messengers (e.g., cAMP, cGMP, $IP_3$, DAG, or $Ca^{2+}$), ion flux, phosphorylation levels, transcription levels, neurotransmitter levels, and the like. Furthermore, such assays can be used to test for inhibitors of the receptors as is well known in the art.

Samples or assays that are treated with a potential receptor inhibitor may be compared to control samples without the test compound, to examine the extent of modulation. Control samples (untreated with inhibitors) are assigned a relative receptor activity value of 100. Inhibiton of receptor activity is achieved when the receptor activity value relative to the control is lower, and conversely receptor activity is enhanced when activity relative to the control is higher.

The effects of the test compounds upon the function of the receptors can be measured by examining any of the parameters described above. Any suitable physiological change that affects receptor activity can be used to assess the influence of a test compound on the coupling of receptors to G-proteins of this invention. When the functional consequences are determined using intact cells or animals, one can measure a variety of effects such as changes in intracellular secondary messengers such as $Ca^{2+}$, $IP_3$ or cAMP. Suitable assays for making such measurements are described in WO 01 18050 which is hereby incorporated by reference.

Preferred assays for G-protein coupled receptors include cells that are loaded with ion sensitive dyes to report receptor activity, as are more fully set out in "G-protein coupled receptors (Signal Transduction Series)", CRC Press 1999; $1^{st}$ Edition; Eds Haga and Berstein, which is incorporated herein by reference. In assays for identifying modulatory compounds, changes in the level of ions in the cytoplasm or membrane voltage will be monitored using an ion sensitive or membrane voltage fluorescent indicator, respectively.

Receptor activation typically initiates subsequent intracellular events, e.g., increases in second messengers such as $IP_3$, which releases intracellular stores of calcium ions. Activation of some G-protein coupled receptors stimulates the formation of inositol triphosphate ($IP_3$) through phospholipase C-mediated hydrolysis of phosphatidylinositol (Berridge & Irvine, Nature 312:315-21 (1984)).

$IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores.

In a preferred embodiment, receptor activity is measured by expressing the receptor in a cell with a G-protein as defined herein above, that links the receptor to a phospholipase C signal transduction pathway. Optionally the cell line is HEK-293, although other mammalian cells are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging.

In yet another embodiment, the ligand-binding domains of the receptors can be employed in vitro in soluble or solid-state reactions to assay for ligand binding. Ligand binding in a receptor, or a domain of a receptor, can be tested in solution, in a bilayer membrane attached to a solid phase in a lipid monolayer or vesicles. Thereby, the binding of a modulator to the receptor, or domain, can be observed using changes in spectroscopic characteristics, e.g. fluorescence, absorbance or refractive index; or hydrodynamic (e.g. shape), chromatographic, or solubility properties, as is generally known in the art.

The compounds tested as modulators of receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make pre-selection of interesting compounds. Some preferred compounds have been set forth herein above. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention.

Lead compounds found by assay technology herein above described, or development compounds formed from such leads can be administered directly to a human subject to modulate taste. Alternatively, such compounds can be formulated with other ingredients of preparations to be taken orally, for example, foods and beverages, pharmaceutical or neutraceutical or homeopathic preparations.

The amount of compound to be taken orally must be sufficient to effect a beneficial response in the human subject, and will be determined by the efficacy of the particular taste modulators and the existence, nature, and extent of any adverse side-effects that accompany the administration of a particular compound.

There now follows a series of examples that serve to illustrate the invention.

For all examples, HEK293 cells were used; for transient transfection of the receptors, HEK293T cells were used, and for stable transfection of the receptors, T-Rex™ HEK293 cells (Invitrogen Corp., Carlsbad, Calif.) were used.

EXAMPLE 1

Production of $G_{\alpha 16\text{-}gustducin44}$ Chimera

The $G_{\alpha 16gustducin44}$ was constructed by bridge overlap PCR mutagenesis using the human $G_{\alpha 16}$ and rat gustducin cDNAs in pcDNA3.1 as templates with T7 and SP6 promoter sequences as outer flanking primer regions. Gene specific primers used were:

```
16gust44-S:
(5' GGCCCCGAGGGCAGCAACTTAAAAAAAGAAGATAAGGAA 3')

16gust44-AS:
(5' TTCCTTATCTTCTTTTTTTAAGTTGCTGCCCTCGGGGCC 3')
```

First, two overlapping PCR fragments that correspond to $G_{\alpha 16}$ and gustducin were amplified. The 5' $G_{\alpha 16}$ fragment was made using the T7 primer in conjunction with the 16gust44-AS primer, whereas the 3' gustducin fragment was made using the SP6 primer in conjunction with the 16gust44-S primer. The individual PCR products were separated by agarose gel electrophoresis and purified. The purified PCR products were mixed, annealed together and then the full-length chimeric fragments were amplified using T7 and SP6 primers. 1.5 mM $MgCl_2$ was included in the PCR mixtures and the PCR products were amplified with thermal cycling parameters at 94° C. for 45 s, 50° C. for 90 s and 72° C. for 120 s using a GeneAmp PCR System 9700 from Applied Biosystems. The assembled chimeric PCR fragment was subcloned into pcDNA3.1 and checked for integrity by DNA sequencing and restriction mapping. Proper expression of the fusion protein was confirmed via Western blot analysis of whole cell lysates from transfected cells using an anti-$G_{\alpha 16}$ polyclonal antibody (Torrey Pines Biolabs).

EXAMPLE 2

Fluo-4 Calcium Assay

All assays are performed using black, clear-bottom 96-well plates that have been seeded the day before with 20K transfected cells per well and have been maintained at 37 degrees C. overnight in appropriate growth media. At the time of the assay, the growth media is discarded and cells are incubated for 1 hour (at room temperature in the dark) with 75 µl of a calcium assay solution consisting of 1.5 µM Fluo-4 AM (Molecular Probes) and 2.5 mM probenicid (Sigma-Aldrich) dissolved in a Hanks balanced salts solution (HBSS) that has been supplemented with 10 mM Hepes, 200 µM calcium chloride and 0.1% bovine serum albumin, pH 7.4 at 37 degrees C. After the initial 1 hour loading period, 125 µl of wash buffer consisting of 2.5 mM probenicid dissolved in HBSS that has been supplemented with 10 mM Hepes, 200 µM calcium chloride and 0.1% bovine serum albumin, pH 7.4 at 37 degrees C., is added to each well and the plate is further incubated for 30 minutes at room temperature in the dark to allow for complete deesterification of the Fluo-4-AM. The buffer solutions are discarded, the plate is washed 3 times with 100 µl wash buffer and finally the cells are reconstituted in 200 µl of wash buffer and incubated for 15 minutes at 37 degrees C. For assay reading, the plate is placed in a fluorescent microplate reader, for example the Flexstation (Molecular Devices), and receptor activation is initiated following addition of 20 µl of a 10× concentrated ligand stock solution. Fluorescence is continuously monitored for 15 seconds prior to ligand addition and for 45-75 seconds after ligand addition. Receptor activation levels are defined as by the two following equations: % Activation=(Maximum fluorescence−baseline fluorescence/baseline fluorescence)*100 or Fluorescence Increase=Maximum Fluorescence−baseline fluorescence, where baseline fluorescence represents the average fluorescence levels prior to ligand addition.

EXAMPLE 3

Transfections for T2R Bitter Receptors

At day 0, cells stably expressing the G-protein are plated in black, clear-bottom 96-well plate at 20,000 cells per well and grown overnight in selective growth media. On day 1, the media is changed to an antibiotic-free growth media and the cells are transfected using 300 ng GPCR DNA and 0.6 µl of Lipofectamine 2000 (Invitrogen). The cells are grown overnight and processed the next day using the Fluo-4 calcium assay conditions described in Example 2 above.

EXAMPLE 4

Transfections for T1R Sweet Receptors

At day 0, cells stably expressing the G-protein are plated in a 6-well plate at a density of 800,000-950,000 cells per well and grown overnight in selective growth media. On day 1, the media is changed to an antibiotic-free growth media and the cells are transfected using 2 µg of T1R2 and 2 µg of T1R3 cDNA and 10 µl of Lipofectamine 2000 (Invitrogen). The cells are maintained overnight in antibiotic-free growth media. On day 2, the cells are replated into a black, clear-bottom 96 well plate at 20,000 cells per well and grown overnight. The morning of the calcium assay, the media is replaced with low glucose media supplemented with Glutamax and dialyzed FBS to minimize receptor desensitization by sugars and glutamate. The cells are further incubated in this media for 6 hours at 37 degrees C. At the end of this period, the cells are processed for the calcium assay according to conditions described above.

EXAMPLE 5

Activation of Human TAS2R16 by a Bitter Glucoside in Cells Expressing Different G-Proteins.

5 mM of phenyl-β-D-glucopyranoside was added in cells expressing hTAS2R16 and either wild-type $G_{\alpha16}$, a chimera of the invention $G_{\alpha16gustducin44}$, and a comparative chimera $G_{\alpha16z44}$. Cells stably expressing the different G-proteins were transiently transfected for 24 hours with the human TAS2R16 bitter receptor. Following transfection, the cells were treated with Fluo-4 and intracellular calcium fluorescence was measured as described above in Example 2. Cellular fluorescence was monitored constantly and the mean fluorescence measured for 15 seconds prior to ligand addition was considered as the baseline, non-stimulated level of fluorescence. Cells expressing the $G_{\alpha16gustducin44}$ chimera displayed a greater degree of receptor activation following ligand stimulation than cells expressing $G_{\alpha16}$.

TABLE 1

Functional activity of human bitter receptor with G-protein variants

| Taste Receptor | Promiscuous G-protein | | |
|---|---|---|---|
| | $G_{\alpha16gustducin44}$ | $G_{\alpha16}$ | $G_{\alpha16z44}$ |
| sham transfected (control) | 2162 | 1024 | 1541 |
| human TAS2R16 | 23821 | 3494 | 8296 |

All data are expressed in relative fluorescence units (RFUs) and represents the increase in mean fluorescence over baseline following ligand addition. The ligand and final concentration used was 5 mM phenyl-β-D-glucopyranoside. Similar results were also obtained using 5 mM D-salicin.

EXAMPLE 6

Functional Activity of Mouse Bitter Receptor (T2R5) with G-Proteins

Following the methodology as described in Example 5 the following results were obtained:—

TABLE 2

| Taste Receptor | Promiscuous G-protein | |
|---|---|---|
| | $G_{\alpha16gustducin44}$ | $G_{\alpha16}$ |
| sham transfected (control) | 3989 | 1705 |
| mouse T2R5 | 10407 | 2569 |

All data are expressed in relative fluorescence units (RFUS) and represents the increase in mean fluorescence over baseline following ligand addition. The ligand and final concentration used was 10 µM cycloheximide.

EXAMPLE 7

Activation of Human Bitter Receptor TAS2R10 by Strychnine in Cells Stably Expressing $G_{\alpha16gustducin44}$ and TAS2R10

The example was performed essentially as described in example 5, except that tetra-cycline-inducible cell lines stably expressing human TAS2R10 and G16gust44 were used instead of transient transfection. Cells were kept at a cell density of 75-80%. The following results were obtained:

TABLE 3

| Taste Receptor | Promiscuous G-protein $G_{\alpha16gustducin44}$ |
|---|---|
| G-protein only(control w/o tetracycline) | 13238 |
| G-protein + human TAS2R10 (with tetracycline) | 24280 |

All data are expressed in relative fluorescence units (RFUs) and represents the increase in mean fluorescence over baseline following ligand addition. The ligand and final concentration used was 250 µM strychnine.

EXAMPLE 8

Activation of Human Bitter Receptor TAS2R38 by Phenylthiocarbamide or Propythiouracil in Cells Stably Expressing $G_{\alpha16gustducin44}$ and TAS2R38

The example was performed essentially as described in example 5, except that tetracycline-inducible cell lines stably expressing human TAS2R38 and G16gust44 were used instead of transient transfection. Cells were kept at a cell density of 75-80%. The following results were obtained:

TABLE 4

| Taste Receptor | Promiscuous G-protein $G_{\alpha16gustducin44}$ |
|---|---|
| G-protein only(control w/o tetracycline) | 3422 |
| G-protein + human TAS2R38 (with tetracycline) | 8989 |

All data are expressed in relative fluorescence units (RFUs) and represents the increase in mean fluorescence over baseline following ligand addition. The ligand and final concentration used was 250 µM phenylthiocarbamide. Similar results were obtained using 250 µM propythiouracil.

EXAMPLE 9

Functional Activity of Human Bitter Receptor (TAS2R43) with G-Proteins.

Using similar methodology as Example 5 except that tetracycline-inducible cell lines stably expressing human TAS2R43 and G16gust44 were used instead of transient Transfection. Cells were kept at a cell density of 75-80%. The following results were obtained:

TABLE 5

| Taste Receptor | Promiscuous G-protein $G_{\alpha16gustducin44}$ |
|---|---|
| G-protein only | 3955 |
| G-protein + human TAS2R43 | 26766 |

All data are expressed in relative fluorescence units (RFUs) and represents the increase in mean fluorescence over baseline following ligand addition. The ligand and final concentration used was 10 µM aristolochic acid.

EXAMPLE 10

Functional Activity of Human Bitter Receptor (TAS2R44) with G-Proteins.

Using similar methodology as Example 5 except that tetracycline-inducible cell lines stably expressing human TAS2R44 and G16gust44 were used instead of transient Transfection. Cells were kept at a cell density of 75-80%. The following results were obtained:

TABLE 6

| Taste Receptor | Promiscuous G-protein $G_{\alpha 16gustducin44}$ |
|---|---|
| G-protein only | 5700 |
| G-protein + human TAS2R44 | 17254 |

All data are expressed in relative fluorescence units (RFUS) and represents the increase in mean fluorescence over baseline following ligand addition. The ligand and final concentration used was 10 μM aristolochic acid.

EXAMPLE 11
Functional Activity of Human Sweet Receptor with G-Proteins

Following the methodology as described in Example 5 the following results were obtained:—

TABLE 7

| Taste Receptor | Promiscuous G-protein | |
|---|---|---|
| | $G_{\alpha 16gustducin44}$ | $G_{\alpha 15}$ |
| sham transfected (control) | 1370 | 643 |
| human TAS1R2/TAS1R3 | 4617 | 1300 |

All data are expressed in relative fluorescence units (RFUS) and represents the increase in mean fluorescence over baseline following ligand addition. The ligand and final concentration used was 2.5 mM sucralose. Similar results were also obtained using 2.5 mM aspartame or acesulfame K.

---

The invention claimed is:

1. A Gα16/gust 44 or Gα15/gust44 chimeric G-protein wherein the last 44 amino acids of the Gα16/gust 44 or Gα15/gust44 protein sequence are replaced with a 44 amino acid unit of Gustducin, where such 44 amino acid unit of Gustducin is the last 44 amino acids of SEQ ID NO:2 where the chimeric protein, when employed in a mammalian cell-based assay increases the signal strength to at least double the signal strength of wild type Gα16.

2. A G-protein according to claim 1 encoded for by the nucleic acid set forth in SEQ ID NO:1.

3. A nucleic acid comprising the nucleotide sequence set forth in SEQ ID NO:1 encoding for a G-protein according to claim 1.

4. An expression vector comprising nucleic acid comprising the nucleotide sequence set forth in SEQ ID NO:1 encoding for a G-protein according to claim 1.

5. A host cell transformed with an expression vector according to claim 4.

6. A method of producing a chimeric G-protein according to claim 1 comprising the step of culturing host cells having contained therein an expression vector encoding for the chimeric G-protein, under conditions sufficient for expression of said G-protein, thereby causing production of the protein, and recovering the protein produced by the cell.

7. A method of analysis and discovery of modulators of taste receptors employing a mammalian cell-based assay employing a transfected gene or cDNA encoding a chimeric protein of claim 1 and a taste receptor, the method comprising the steps of contacting a compound with cells, and determining the functional effect of the compound on the chimeric G-protein.

8. The method of analysis and discovery of modulators of taste receptors of claim 7 where the taste receptors are bitter receptors.

9. A method according to claim 6 wherein expression of said G-protein is measured by signal transduction output determined by measuring the changes in intracellular messengers IP3 or calcium$^{2+}$.

10. A Gα16/gust 44 or Gα15/gust44 chimeric G-protein wherein the last 44 amino acids of the Gα16/gust 44 or Gα15/gust44 protein sequence are replaced with a 44 amino acid unit of Gustducin, where such 44 amino acid unit of Gustducin is the last 44 amino acids of SEQ ID NO:2, and wherein the resulting $G_{aq\text{-}gust44}$ chimeric G-protein has a sequence homology of at least 80% in the last 44 amino acids of SEQ ID NO:2 where the chimeric protein, when employed in a mammalian cell-based assay increases the fluorescence signal strength by at least double the signal strength of wild type Gα16.

11. The chimeric G-protein of claim 10 having a sequence homology of at least 90% in the last 44 amino acids of SEQ ID NO:2.

12. The chimeric G-protein of claim 10 having a sequence homology of at least 95% in the last 44 amino acids of SEQ ID NO:2.

13. A nucleic acid encoding for a G-protein according to claim 10.

14. An expression vector comprising nucleic acid comprising the nucleotide sequence encoding for a G-protein according to claim 10.

15. A host cell transformed with an expression vector according to claim 14.

16. A method of producing a chimeric G-protein according to claim 10 comprising the step of culturing host cells having contained therein an expression vector encoding for the chimeric G-protein, under conditions sufficient for expression of said G-protein, thereby causing production of the protein, and recovering the protein produced by the cell.

17. A method of analysis and discovery of modulators of taste receptors using the chimeric proteins of claim 10 employing a mammalian cell-based assay employing a transfected gene or cDNA encoding a chimeric Gα16/gust 44 or Gα15/gust44 G-protein and a taste receptor, the method comprising the steps of contacting a compound with cells, and determining the functional effect of the compound on chimeric G-protein.

18. The method of claim 17 where the taste receptor is a bitter taste receptor.

19. A method according to claim 16 wherein expression of said G-protein is measured by signal transduction output determined by measuring the changes in intracellular messengers IP3 or calcium$^{2+}$.

20. The method of claim 17 where the taste receptor is a sweet taste receptor.

21. The method of claim 17 where the taste receptor is a umami taste receptor.

22. A Gα16/gust 44 or Gα15/gust44 chimeric G-protein wherein the last 44 amino acids of the Gα16/gust 44 or Gα15/gust44 protein sequence are replaced with a 44 amino acid unit of Gustducin, where such 44 amino acid unit of Gustducin is the last 44 amino acids of SEQ ID NO:2, and where the chimeric protein binds to one or more of the human bitter, sweet and umami taste receptors.

23. The method of claim 7 where the receptors are sweet receptors.

24. The method of claim 7 where the receptors are umami receptors.

* * * * *